United States Patent [19]

Murdock

[11] 4,418,078

[45] Nov. 29, 1983

[54] METHOD OF TREATING TUMORS IN WARM-BLOODED ANIMALS

[75] Inventor: Keith C. Murdock, Pearl River, N.Y.

[73] Assignee: American Cyanamid Company, Stamford, Conn.

[21] Appl. No.: 69,672

[22] Filed: Aug. 27, 1979

Related U.S. Application Data

[63] Continuation of Ser. No. 965,114, Nov. 30, 1978, abandoned, which is a continuation-in-part of Ser. No. 873,041, Jan. 30, 1978.

[51] Int. Cl.$^3$ .......................................... H61K 31/135
[52] U.S. Cl. .................................................. 424/330
[58] Field of Search ......................................... 424/330

[56] References Cited

PUBLICATIONS

Chemical Abstracts 72:101862(2)(1970).

Primary Examiner—Jerome D. Goldberg
Attorney, Agent, or Firm—Edward A. Conroy, Jr.

[57] ABSTRACT

This disclosure describes compositions of matter useful as inhibitors of transplanted mouse tumor growth, the active ingredient of said compositions of matter being 1,4-bis(3-aminopropylamino)-5,8-dihydroxyanthraquinone or the non-toxic acid-addition salts thereof.

1 Claim, No Drawings

METHOD OF TREATING TUMORS IN WARM-BLOODED ANIMALS

CROSS REFERENCE TO RELATED APPLICATION

This application is a continuation of my copending application Ser. No. 965,114, filed Nov. 30, 1978, now abandoned, which is a continuation-in-part of my abandoned application Ser. No. 873,041, filed Jan. 30, 1978.

BRIEF SUMMARY OF THE INVENTION

This invention relates to novel compositions of matter useful in mammals. More particularly, it relates to therapeutic compositions containing 1,4-bis(3-aminopropylamino)-5,8-dihydroxyanthraquinone or the non-toxic acid-addition salts thereof which inhibit the growth of transplanted mouse tumors. Also included within the purview of the present invention are the leuco base and tautomer thereof which may be represented by the following general formulae:

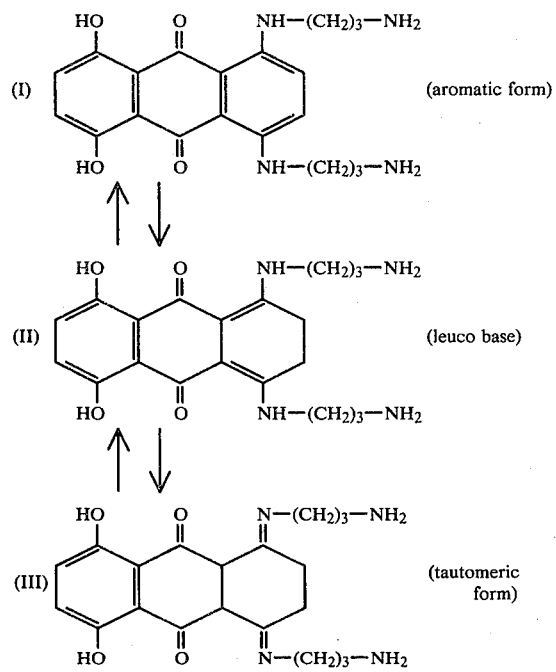

DETAILED DESCRIPTION OF THE INVENTION

The organic bases of this invention (I, II and III) form non-toxic acid-addition salts with a variety of pharmacologically acceptable organic and inorganic salt-forming reagents. Thus, acid-addition salts, formed by admixture of the organic free base with one or two equivalents of an acid, suitably in a neutral solvent, are formed with such acids as sulfuric, phosphoric, hydrochloric, hydrobromic, sulfamic, citric, lactic, malic, succinic, tartaric, acetic, benzoic, gluconic, ascorbic, and the like. For purposes of this invention the free bases are equivalent to their non-toxic acid-addition salts. The acid-addition salts of the organic bases of the present invention are, in general, crystalline solids, relatively soluble in water, methanol and ethanol but relatively insoluble in non-polar organic solvents such as diethyl ether, benzene, toluene and the like.

The active compounds of the present invention possess the property of inhibiting the growth of transplanted mouse tumors as established by the following tests.

Lymphocytic leukemia P388 test

The animals used are $BDF_1$ or $CDF_1$ mice all of one sex, weighing a minimum of 17 g. and all within a 3 g. weight range. There are 5 or 6 animals per test group. The tumor transplant is made by intraperitoneal injection of 0.1 ml. of dilute ascitic fluid containing $10^6$ cells of lymphocitic leukemia P388. The test compounds are administered intraperitoneally on days one, 5 and 9 or one through 9 (relative to tumor inoculation) at various doses. The animals are weighed and survivors are recorded on a regular basis for 30 days. The median survival time and the ratio of survival time for treated (T)/control (C) animals are calculated. The positive control compound is 5-fluorouracil given at 20 or 60 mg./kg. The results of this test with the compound of the present invention appear in Table I. The criterion for efficacy is $T/C \times 100 \geq 125\%$.

TABLE I

Lymphocytic leukemia P388 test

| Compound | Dose (mg./kg.) | Median Survival (Days) | T/C × 100 (Percent) |
|---|---|---|---|
| 1,4-Bis(3-aminopropylamino)-5,8-dihydroxyanthraquinone | 25 | 22.0 | 183 |
| | 12 | 19.0 | 158 |
| Control | 0 | 12.0 | — |
| 5-Fluorouracil | 60 | 19.5 | 162 |

Melanotic melanoma B16 test

The animals used are C57BC/6 mice, all of the same sex, weighing a minimum of 17 g. and all within a 3 g. weight range. There are normally 10 animals per test group. A one gram portion of melanotic melanoma B16 tumor is homogenized in 10 ml. of cold balanced salt solution and implanted intraperitoneally as 0.5 ml. of the homogenate. The test compounds are administered intraperitoneally on days one through 9 (relative to tumor inoculation) at various doses. The animals are weighed and survivors are recorded on a regular basis for 60 days. The median survival time and the ratio of survival time for treated (T)/control (C) animals are calculated. The positive control compound is 5-fluorouracil given at 20 mg./kg. The results of this test with the compound of the present invention appear in Table II. The criterion for efficacy is $T/C \times 100 \geq 125\%$.

TABLE II

Melanotic melanoma B16

| Compound | Dose (mg./kg.) | Median Survival (Days) | T/C × 100 (Percent) |
|---|---|---|---|
| 1,4-Bis(3-aminopropylamino)-5,8-dihydroxyanthraquinone | 12 | 24.0 | 150 |
| | 6 | 30.0 | 187 |
| Control | 0 | 16.0 | — |
| 5-Fluorouracil | 20 | 26.5 | 166 |

Lymphocytic leukemia L1210 test

The animals used were CDF mice, all of one sex, weighing a minimum of 17 grams and all within a 3-gram weight range. There were 5 animals per test group, 10 in control groups. The tumor transplant was by intraperitoneal injection of 0.1 ml. of lymphocytic leukemia L1210 at a concentration of $10^5$ cells/mouse. The test compound was administered intraperitoneally on days one, 5 and 9 (relative to tumor inoculation) at various doses. The animals were weighed and survivors were recorded on a regular basis for 30 days. The median survival time and the ratio of survival time for treated (T)/control (C) animals were calculated. The positive control compound was 5-fluorouracil, doses at 60 mg./kg. of body weight. The results of this test appear in Table III.

TABLE III

| Compound | Dose (mg./kg.) Days 1,5,9 | Mean Survival (Days) | T/C × 100 (Percent) |
|---|---|---|---|
| 1,4-bis(3-amino-propylamino)-5,8-dihydroxyanthra-quinone | 50 | >30 | >353 |
| | 25 | 15 | 176 |
| | 12.5 | 15 | 176 |
| | 6.2 | 14 | 165 |
| | 3.1 | 11 | 129 |
| | 1.56 | 10 | 118 |
| | 0.78 | 9 | 106 |
| Control | 0 | 8.5 | — |
| 5-Fluorouracil | 60 | 14.5 | 171 |

Adriamycin-resistant P-388 leukemia test

The procedure for this test was the same as that described for lymphocytic leukemia L1210 except that the tumor transplant consisted of lymphocytic leukemia P-388 subline resistant to Adriamycin administered at a concentration of $10^6$ cells/mouse. The results of this test appear in Table IV.

TABLE IV

| Compound | Dose (mg./kg.) Days 1,5,9 | Mean Survival (Days) | T/C × 100 (Percent) |
|---|---|---|---|
| 1,4-bis-(3-amino-propylamino)-5,8-dihydroxyanthra-quinone | 50 | 10.0 | 95 |
| | 25 | 17.0 | 162 |
| | 12.5 | 14.0 | 133 |
| | 6.2 | 14.0 | 133 |
| | 3.1 | 14.0 | 133 |
| Control | 0 | 10.5 | — |
| 5-Fluorouracil | 60 | 20 | 190 |

The active ingredients of the present invention inhibit transplanted mouse tumor growth when administered orally in amounts ranging from about 5 mg. to about 200 mg. per kilogram of body weight per day. A preferred dosage regimen for optimum results would be from about 5 mg. of about 50 mg. per kilogram of body weight per day. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active compound may be administered in any convenient manner such as the oral or buccal routes or it may be incorporated directly in the diet.

The active ingredients of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active ingredient in such therapeutically useful compositions is such that a suitable dosage will be obtained. Preferred compositions or preparations according to the present invention are prepared so that an oral dosage unit form contains between about 5 and 200 milligrams of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active ingredients may be incorporated into sustained-release preparations and formulations.

The active ingredients of the present invention may also be administered parenterally or intraperitoneally. Solutions of the active ingredient as a free base or salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active ingredient in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatable with the active ingredient, its use in the present compositions is contemplated. Supplementary active ingredients can also be incorporated into the inventive compositions.

It is especially advantageous to formulate parenteral compositions in dosage unit form for ease of administration and uniformity of dosage. Dosage unit form as used in the specification and claims herein refers to physically discrete units suited as unitary dosages for the mammalian subjects to be treated; each unit containing a predetermined quantity of active material calculated to produce the desired therapeutic effect in association with the required pharmaceutical carrier. The specification for the noval dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as disclosed in detail in this specification.

The dosage of the principal active ingredient for the treatment of the indicated conditions depends upon the age, weight and condition of the subject being treated; the particular condition and its severity; the particular form of the active ingredient and the route of administration. A daily dose of from about 5 to about 200 mg./kg. of body weight given singly or in divided doses of up to 5 times a day embraces the effective range for the treatment of most conditions for which the compound is effective and substantially non-toxic. If the dosage is divided, for example, into 3 individual dosages, these will range from about 125 mg. to about 1.0 g. of the active ingredient.

The principal active ingredient is compounded for convenient and effective administration in effective amounts with a suitable pharmaceutically-acceptable carrier in dosage unit form as hereinbefore disclosed. A unit dosage form can, for example, contain the principal active ingredient in amounts ranging from about 0.1 to about 3.0 g., with from about 0.5 to about 1.0 g. being preferred. Expressed in proportions, the active ingredient is generally present in from about 0.1 to about 400 mg./ml. of carrier. In the case of compositions containing supplementary active ingredients, the dosages are determined by reference to the usual dose and manner of administration of the said ingredients.

Regression and palliation of cancers are attained, for example, using intraperitoneal administration. A single intravenous dosage or repeated daily dosages can be administered. Daily dosages up to about 5 or 10 days are often sufficient. It is also possible to dispense one daily dosage or one dose on alternate or less frequent days.

The invention will be described in greater detail in conjunction with the following specific examples.

EXAMPLE 1

1,4-Bis(3-aminopropylamino)-5,8-dihydroxyanthraquinone

A suspension of 10.0 g. of leuco-1,4,5,8-tetrahydroxyanthraquinone in 120 ml. of de-aerated 1,3-diaminopropane is stirred and heated at 45° C. under nitrogen for one hour and then for 10 minutes as air is bubbled into the suspension. The mixture is then evaporated to dryness and the residue is extracted with 650 ml. of ethanol in a Soxhlet apparatus for 17 hours. The extract is filtered while hot, concentrated to 95 ml. and then diluted with 900 ml. of diethyl ether. The mixture is cooled and the solid is collected, washed with ethanol-diethyl ether, then diethyl ether giving the desired product as 9.57 g. of a blue solid, mp. 115°–130° C.

EXAMPLE 2

| Preparation of 50 mg. Tablets | | |
|---|---|---|
| Per Tablet | | Per 10,000 Tablets |
| 0.050 gm. | 1,4-bis(3-aminopropylamino)-5,8-dihydroxyanthraquinone | 500 gm. |
| 0.080 gm. | Lactose | 800 gm. |
| 0.010 gm. | Corn Starch (for mix) | 100 gm. |
| 0.008 gm. | Corn Starch (for paste) | 75 gm. |
| 0.148 gm. | | 1475 gm. |
| 0.002 gm. | Magnesium Stearate (1%) | 15 gm. |
| 0.150 gm. | | 1490 gm. |

The 1,4-bis(3-aminopropylamino)-5,8-dihydroxyanthraquinone, lactose and corn starch (for mix) are blended together. The corn starch (for paste) is suspended in 600 ml. of water and heated with stirring to form a paste. This paste is then used to granulate the mixed powders. Additional water is used if necessary. The wet granules are passed through a No. 8 hand screen and dried at 120° F. The dry granules are then passed through a No. 16 screen. The mixture is lubricated with 1% magnesium stearate and compressed into tablets in a suitable tableting machine.

EXAMPLE 3

| Preparation of Oral Suspension | |
|---|---|
| Ingredient | Amount |
| Leuco-1,4-bis(3-aminopropylamino)-5,8-dihydroxyanthraquinone | 500 mg. |
| Sorbitol solution (70% N.F.) | 40 ml. |
| Sodium benzoate | 150 mg. |
| Saccharin | 10 mg. |

-continued

| Preparation of Oral Suspension | |
|---|---|
| Ingredient | Amount |
| Red dye | 50 mg. |
| Cherry flavor | 50 ml. |
| Distilled water qs ad | 100 ml. |

The sorbitol solution is added to 40 ml. of distilled water and the leuco-1,4-bis(3-aminopropylamino)-5,8-dihydroxyanthraquinone is suspended therein. The saccharin, sodium benzoate, flavor and dye are added and dissolved. The volume is adjusted to 100 ml. with distilled water. Each ml. of syrup contains 5 mg. of leuco-1,4-bis(3-aminopropylamino)-5,8-dihydroxyanthraquinone.

EXAMPLE 4

Preparation of Parenteral Solution

In a solution of 700 ml. of propylene glycol and 200 ml. of water for injection is suspended 20.0 grams of 1,4-bis(3-aminopropylamino)-5,8-dihydroxyanthraquinone dihydrochloride with stirring. After suspension is complete, the pH is adjusted to 5.5 with hydrochloric acid and the volume is made up to 1000 ml. with water for injection. The formulation is sterilized, filled into 5.0 ml. ampoules each containing 2.0 ml. (representing 40 mg. of drug) and sealed under nitrogen.

I claim:

1. A pharmaceutical composition in dosage unit form comprising from about 5 to about 200 milligrams of a compound selected from the group consisting of 1,4-bis(3-aminopropylamino)-5,8-dihydroxyanthraquinone, the leuco base or tautomer thereof, and the pharmacologically acceptable acid-addition salts thereof; in association with a pharmaceutical carrier.

* * * * *